(12) United States Patent
Hayama et al.

(10) Patent No.: US 7,824,449 B2
(45) Date of Patent: Nov. 2, 2010

(54) HAIR DYE COMPOSITION

(75) Inventors: Miyuki Hayama, Sumida-ku (JP);
Osamu Takiguchi, Sumida-ku (JP);
Yoshimasa Tate, Sumida-ku (JP);
Masaaki Tsukase, Minamiashigara (JP)

(73) Assignees: Kao Corporation, Tokyo (JP);
FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/527,750

(22) PCT Filed: Apr. 25, 2008

(86) PCT No.: PCT/JP2008/058454
§ 371 (c)(1),
(2), (4) Date: Aug. 19, 2009

(87) PCT Pub. No.: WO2008/139985
PCT Pub. Date: Nov. 20, 2008

(65) Prior Publication Data
US 2010/0115710 A1    May 13, 2010

(30) Foreign Application Priority Data
Apr. 26, 2007   (JP) .............................. 2007-116588

(51) Int. Cl.
*A61Q 5/10* (2006.01)
*C07C 245/00* (2006.01)

(52) U.S. Cl. ....................... 8/405; 8/565; 8/566; 8/570; 8/574; 534/551

(58) Field of Classification Search ..................... 8/405, 8/565, 566, 570, 574; 534/551
See application file for complete search history.

(56) References Cited

U.S. PATENT DOCUMENTS

| | | | |
|---|---|---|---|
| 5,328,993 A * | 7/1994 | Furstenwerth et al. | ...... 534/551 |
| 7,232,467 B2 | 6/2007 | Adam et al. | |
| 7,476,261 B2 | 1/2009 | Yamaguchi et al. | |
| 2008/0134448 A1 | 6/2008 | Yamaguchi et al. | |

FOREIGN PATENT DOCUMENTS

| | | |
|---|---|---|
| EP | 0 071 901 | 2/1983 |
| JP | 53 043324 | 11/1978 |
| JP | 6-271435 | 9/1994 |
| JP | 2006-511721 | 4/2006 |
| JP | 2006-182653 | 7/2006 |
| WO | 2006 068104 | 6/2006 |

OTHER PUBLICATIONS

STIC Search Report dated May 20, 2010.*

* cited by examiner

*Primary Examiner*—Eisa B Elhilo
(74) *Attorney, Agent, or Firm*—Oblon, Spivak, McClelland, Maier & Neustadt, L.L.P.

(57) ABSTRACT

A hair dye composition containing a triazene dissociative direct dye represented by general formula (1): A-N=N—NH-B (1) wherein A and B are each a monocyclic or a bicyclic aromatic heterocyclic group that may have a substituent or a monocyclic or a bicyclic aryl group that may have a substituent and contain none of a carboxy group, a sulfo group and a quaternary ammonium group; and A and B each bind to a triazene-1,3-diyl group represented by —N=N—NH— via a carbon atom within A and B each. A and B may be the same or different.

3 Claims, No Drawings

HAIR DYE COMPOSITION

FIELD OF THE INVENTION

The present invention relates to a hair dye composition containing a dissociative direct dye.

BACKGROUND OF THE INVENTION

As typical hair dye compositions, mention may be made of a two-part permanent hair dye composition composed of a first part containing an alkaline agent, an oxidation dye and optionally a direct dye such as a nitro dye and a second part containing an oxidizing agent; and a single-part semi-permanent hair dye composition containing an organic acid or an alkaline agent, and at least one type of direct dye such as an acid dye, a basic dye and a nitro dye.

The permanent hair dye has a drawback in that the color tone of hair imparted by an oxidation dye is not so vibrant. Attempts to use a direct dye in combination with an oxidation dye are generally, made to obtain vibrant color. However, a direct dye, in particular, a nitro dye, has a problem in that the color of hair dyed significantly fades. More specifically, the color tone of the hair, even if it is vibrant immediately after dyeing, quickly loses vibrantness (see, for example, Patent Document 1).

A direct dye to be used in combination with an oxidation dye must be stable to a peroxide during a hair-dyeing process. For this reason, the range of direct dyes is limited.

In any one of acid dyes, basic dyes and nitro dyes used in permanent hair dyes and semi-permanent hair dyes, the color of hair quickly fades because the hair loses a direct dye therefrom by washing and exposure to light. This phenomenon is significantly seen in damaged hair.

In such circumstance, as one of the solutions to deal with resistance (fastness) to light, washing, perspiration, friction and heat, it has been proposed to use a direct dye having a dissociative proton in a hair dye (Patent Document 2). The dissociative proton is derived from a phenolic hydroxy group. When a proton is dissociated, anion species are produced, which will contribute to fastness. However, a phenolic hydroxy group dissociates within limited conditions. The limited conditions are also applied to a hair dye composition. Such a limitation can be avoided if a triazene compound having a triazene-1,3-diyl group, which dissociates in different conditions from a phenolic hydroxy group, is used in combination. However, hair dyes containing a triazene compound presently known are not concerned with such dissociation and fail to have excellent fastness (Patent Document 3). In this technical proposal, a hair dye contains a triazene compound not as a direct dye. The proposal only provides a method in which a triazene compound is applied to hair in combination with a water soluble coupling component (a secondary component) and thereafter reacted with the coupling component to produce a compound, which is used as a dye.

[Patent Document 1] JP-A-6-271435
[Patent Document 2] JP-A-2006-182653
[Patent Document 3] JP-A-2006-511721

SUMMARY OF THE INVENTION

According to the present invention, there is provided a hair dye composition containing a triazene dissociative direct dye represented by general formula (1):

$$A-N=N-NH-B \quad (1)$$

wherein A and B are each a monocyclic or a bicyclic aromatic heterocyclic group that may have a substituent or a monocyclic or a bicyclic aryl group that may have a substituent and contain none of a carboxy group, a sulfo group and a quaternary ammonium group; and A and B each bind to a triazene-1,3-diyl group represented by —N=N—NH— via a carbon atom within A and B each. A and B may be the same or different.

According to the present invention, there is further provided a method of dyeing hair by applying the aforementioned hair dye composition to hair.

DETAILED DESCRIPTION OF THE INVENTION

The present invention relates to a hair dye composition capable of imparting vibrant color firmly to hair without decomposing a dye, having excellent fastness to light, washing, perspiration, friction and heat, stability to an alkaline agent and an oxidizing agent, excellent dyeing power and being less color fade with the passage of time; and relates to a method for dyeing hair by use of the hair dye composition.

The present inventors found that a hair dye composition using a predetermined triazene dissociative direct dye satisfies the aforementioned requirements.

In the general formula (1), the monocyclic or bicyclic aromatic heterocyclic group of A and B preferably contains at least one type of hetero atom selected from an oxygen atom, a sulfur atom and a nitrogen atom, within the ring. The monocyclic aromatic heterocyclic group is preferably a 5-membered group. The bicyclic aromatic heterocyclic group is preferably a condensed ring of a 5- or 6-membered ring and a 5- or 6-membered ring. The number of carbon atoms of the aromatic heterocyclic group is preferably 2 to 20, and more preferably, 2 to 10.

The monocyclic or bicyclic aryl group is preferably a monocyclic 6-membered aryl group or a bicyclic aryl group formed by condensation of a monocyclic 6-membered aryl group with another ring. The "another ring" used herein is preferably a 5-membered ring or a 6-membered ring. The number of carbon atoms of the aryl group is preferably 6 to 20, and more preferably, 6 to 12.

The number of substituents that the aromatic heterocyclic group and aryl group may have may be two or more. The substituents of two or more may be the same or different. The substituents positioned next to each other may join to form a saturated or unsaturated 5-membered or 6-membered ring structure. The ring structure thus formed may be a heterocyclic or a carbon ring and a saturated or unsaturated ring. The total number of carbon atoms and hetero atoms of the ring structure to be formed is preferably 3 to 6, and more preferably, 5 or 6.

Examples of the substituents that the aromatic heterocyclic group and aryl group may have include
  a halogen atom (such as a fluorine atom, a chlorine atom or a bromine atom),
  a hydroxy group,
  an amino group,
  a mercapto group,
  an alkyl group (a straight, branched or cyclic alkyl group having 1 to 15, preferably 1 to 6 carbon atoms, such as a methyl group, an ethyl group, an n-propyl group, an isopropyl group, a t-butyl group, an n-octyl group, a 2-ethylhexyl group or a cyclohexyl group),
  an alkenyl group (a straight, branched or cyclic alkenyl group having 2 to 10, preferably 2 to 6 carbon atoms, such as a vinyl group, an allyl group, a prenyl group or a cyclopenten-1-yl group), an alkynyl group (an alkynyl group having 2 to 10, preferably 2 to 6 carbon atoms, such as an ethynyl group or a propargyl group), an aryl group (an aryl group having 6 to 16, preferably 6 to 10 carbon atoms, such as a phenyl group, a p-tolyl group or a naphthyl group), a heterocyclic group (a monovalent group having 1 to 12, preferably 2 to 6 carbon atoms obtained by removing a single hydrogen atom from a 5-membered or 6-membered aromatic or non-aromatic heterocyclic compound, such as a 1-pyrazolyl group, a 1-imidazolyl group, a 2-furyl group, a 2-thienyl group, a 4-pyrimidinyl group, a 2-pyridyl group or a 2-benzothiazolyl group), a nitro group, a cyano group, a carbamoyl group, a sulfamoyl group, an acyl group (a formyl group, an acylalkylcarbonyl group having 2 to 10, preferably 2 to 6 carbon atoms or an arylcarbonyl group having 7 to 12, preferably 7 to 9 carbon atoms, such as a formyl group, an acetyl group, a pivaloyl group or a benzoyl group), an alkoxycarbonyl group (an alkoxycarbonyl group having 2 to 10, preferably 2 to 6 carbon atoms, such as a methoxycarbonyl group, an ethoxycarbonyl group, a t-butoxycarbonyl group or an isobutoxycarbonyl group), an aryloxycarbonyl group (an aryloxycarbonyl group having 7 to 12, preferably 7 to 9 carbon atoms, such as a phenoxycarbonyl group or a naphthoxycarbonyl group), a heterocyclic oxycarbonyl group (a heterocyclic oxycarbonyl group having 1 to 12, preferably 2 to 6 carbon atoms, such as a 1-pyrazolyloxycarbonyl group, a 1-imidazolyloxycarbonyl group, a 2-furyloxycarbonyl group, a 2-thienyloxycarbonyl group, a 2-tetrahydrofuryloxycarbonyl group or a 2-morpholyloxycarbonyl group), an imido group (an imido group having 2 to 10, preferably 4 to 8 carbon atoms, such as an N-succinimide group or an N-phthalimide group), an alkylsulfinyl group (an alkylsulfinyl group having 1 to 10, preferably 1 to 6 carbon atoms, such as a methylsulfinyl group or an ethylsulfinyl group), an arylsulfinyl group (an arylsulfinyl group having 6 to 12, preferably 6 to 8 carbon atoms, such as a phenylsulfinyl group), an alkylsulfonyl group (an alkylsulfonyl group having 1 to 10, preferably 1 to 6 carbon atoms, such as a methylsulfonyl group, an ethylsulfonyl group or a cyclohexylsulfonyl group), an arylsulfonyl group (an arylsulfonyl group having 6 to 12, preferably 6 to 8 carbon atoms, such as a phenylsulfonyl group), a heterocyclic sulfonyl group (a heterocyclic sulfonyl having 1 to 12, preferably 2 to 6 carbon atoms, such as a 2-tetrahydropyranylsulfonyl group), a phosphino group (a phosphino group having 2 to 12, preferably 2 to 6 carbon atoms, such as a dimethylphosphino group or a diphenylphosphino group), and a phosphinyl group (a phosphinyl group having 2 to 12, preferably 2 to 6 carbon atoms, such as a phosphinyl group or a diethoxyphosphinyl group).

Furthermore, these substituents may further have 1 or 2 or more substituents. In this case, examples of the substituents are the same as those exemplified above. In the case where 2 or more substituents are present, they may be the same or different.

Examples of the substituent that may further have a substituent, include an alkyl group or aryl group having a substituent, such as an aralkyl group (an aralkyl group having 7 to 18, preferably 7 to 12 carbon atoms, such as a benzyl group or a phenethyl group), a haloalkyl group (a straight, branched or cyclic alkyl group having 1 to 15, preferably 1 to 6 carbon atoms, such as a chloromethyl group, a 2-chloroethyl group, a 2-bromopropyl group or a 3-bromopropyl group), a haloaryl group (a haloaryl group having 6 to 12, preferably 6 to 8 carbon atoms, such as a p-chlorophenyl group, a 2,4-dichlorophenyl group or a 3-fluorophenyl group), or a hydroxyalkyl group (a straight, branched or cyclic alkyl group having 1 to 15, preferably 1 to 6 carbon atoms, such as a hydroxymethyl group, a 2-hydroxyethyl group, a 2-hydroxypropyl group or a 3-hydroxypropyl group);

a hydroxy group having a substituent, such as an alkoxy group (a straight, branched or cyclic alkoxy group having 1 to 10, preferably 1 to 6 carbon atoms, such as a methoxy group, an ethoxy group, an isopropoxy group, a t-butoxy group, a cyclopentyloxy group or a 2-buten-1-yloxy group), an aryloxy group (an aryloxy group having 6 to 12, preferably 6 to 10 carbon atoms, such as a phenoxy group, a 2-methylphenoxy group or a 4-t-butylphenoxy group), a silyloxy group (a silyloxy group having 3 to 10, preferably 3 to 6 carbon atoms, such as a trimethylsilyloxy group or a t-butyldimethylsilyloxy group), a heterocyclic oxy group (a heterocyclic oxy group having 1 to 12, preferably 2 to 6 carbon atoms, such as a 1-phenyltetrazole-5-oxy group or a 2-tetrahydropyranyloxy group), an alkylsulfonyloxy group (a straight, branched or cyclic alkylsulfonyloxy group having 1 to 10, preferably 1 to 6 carbon atoms, such as a methanesulfonyloxy group or an ethanesulfonyloxy group), an arylsulfonyloxy group (an arylsulfonyloxy group having 6 to 12, preferably 6 to 10 carbon atoms, such as a phenylsulfonyloxy group), a heterocyclic sulfonyloxy group (a heterocyclic sulfonyloxy group having 1 to 12, preferably 2 to 6 carbon atoms, such as a 2-pyridylsulfonyloxy group), an acyloxy group (an acyloxy group having 1 to 12, preferably 1 to 8 carbon atoms, such as a formyloxy group, an acetyloxy group, a pivaloyloxy group or a benzoyloxy group), a carbamoyloxy group (a carbamoyloxy group having 1 to 10, preferably 1 to 6 carbon atoms, such as an N,N-dimethylcarbamoyloxy group, an N,N-diethylcarbamoyloxy group or a morpholinocarbonyloxy group), an alkoxycarbonyloxy group (an alkoxycarbonyloxy group having 2 to 10, preferably 2 to 8 carbon atoms, such as a methoxycarbonyloxy group, an ethoxycarbonyloxy group, a t-butoxycarbonyloxy group or an n-octyloxycarbonyloxy group), an aryloxycarbonyloxy group (an aryloxycarbonyloxy group having 7 to 12, preferably 7 to 10 carbon atoms, such as a phenoxycarbonyloxy group or a p-methoxyphenoxycarbonyloxy group), or a phosphinyloxy group (a phosphinyloxy group having 2 to 12, preferably 2 to 6 carbon atoms, such as a diphenoxyphosphinyloxy group or a dibutoxyphosphinyloxy group);

an amino group having a substituent such as an alkylamino group (an alkylamino group having 1 to 20, preferably 1 to 12 carbon atoms, such as a methylamino group, a dimethylamino group or a cyclohexylmethylamino group)

an arylamino group (an arylamino group having 6 to 16, preferably 6 to 12 carbon atoms, such as an anilino group, an N-methylanilino group or a diphenylamino group), a heterocyclic amino group (a heterocyclic amino group having 1 to 12, preferably 2 to 6 carbon atoms, such as a 2-pyridylamino group, a pyrazol-4-yl amino group, a benzimidazol-2-yl amino group, a benzothiazol-2-yl amino group, a benzoxazol-2-yl amino group, a 2-oxazolyl amino group, 1,2,4-triazol-3-yl amino group, a 1,2,4-thiadiazol-2-yl amino group, a 1,3,4-thiadiazol-2-yl amino group, a 1,2,4-oxadiazol-2-yl amino group, or a 1,3,4-oxadiazol-2-yl amino group), an acylamino group (an alkylcarbonylamino group having 1 to 10, preferably 1 to 6 carbon atoms, preferably an arylcarbonylamino group having 6 to 18, preferably 6 to 12 carbon atoms, or a heterocyclic carbonylamino group having 2 to 12, preferably 2 to 6 carbon atoms, such as a formylamino group, an acetylamino group, a pivaloylamino group, a benzoylamino group, a pyridine-4-carbonylamino group or a thiophene-2-carbonylamino group), a ureido group (an aminocarbonylamino group having 1 to 12, preferably 1 to 8 carbon atoms, such as a carbamoylamino group, an N,N-dimethylaminocarbonylamino group, an N,N-diethylaminocarbonylamino group, a morpholin-4-ylcarbonylamino group), an alkoxycarbonylamino group (an alkoxycarbonylamino group having 2 to 10, preferably 2 to 6 carbon atoms, such as a methoxycarbonylamino group, an ethoxycarbonylamino group or a t-butoxycarbonylamino group), an aryloxycarbonylamino group (an aryloxycarbonylamino group having 7 to 12, preferably 7 to 9 carbon atoms, such as a phenoxycarbonylamino group), a heterocyclic oxycarbonylamino group (an heterocyclic oxycarbonylamino group having 1 to 12, preferably 2 to 6 carbon atoms, such as a 2-pyridyloxycarbonylamino group), a sulphamoylamino group (a sulphamoylamino group having 0 to 10, preferably 0 to 6 carbon atoms, such as a sulphamoylamino group or an N,N-dimethylaminosulfonylamino group, an alkylsulfonylamino group (an alkylsulfonylamino group having 1 to 10, preferably 1 to 6 carbon atoms, such as a methylsulfonylamino group, an ethylsulfonylamino group or an n-butylsulfonylamino group), an arylsulfonylamino group (an arylsulfonylamino group having 6 to 12, preferably 6 to 8 carbon atoms, such as a phenylsulfonylamino group), or a phosphinylamino group (a phosphinylamino group having 2 to 12, preferably 2 to 6 carbon atoms, such as a dimethoxyphosphinylamino group or a dimethylaminophosphinylamino group);

a mercapto group having a substituent such as an alkylthio group (an alkylthio group having 1 to 10, preferably 1 to 6 carbon atoms, such as a methylthio group, an ethylthio group or a butylthio group), an arylthio group (an arylthio group having 6 to 12, preferably 6 to 8 carbon atoms, such as a phenylthio group), or a heterocyclic thio group (a heterocyclic thio group having 2 to 10, preferably 1 to 6 carbon atoms, such as a -2-benzothiazolylthio group or a 1-phenyltetrazol-5-ylthio group);

a carbamoyl group having a substituent such as an alkylcarbamoyl group (a alkylcarbamoyl group having 2 to 12, preferably 2 to 8 carbon atoms, such as a methylcarbamoyl group, a dimethylcarbamoyl group or a dibutylcarbamoyl group), or a sulfamoylcarbamoyl group (a sulfamoylcarbamoyl group having 1 to 12, preferably 1 to 8 carbon atoms, such as an N-(sulfamoyl)carbamoyl group or an N-(N', N'-dimethylsulfamoyl)carbamoyl group);

a sulfamoyl group having a substituent such as an alkylsulfamoyl group (an alkylsulfamoyl group having 1 to 12, preferably 1 to 6 carbon atoms, such as an ethylsulfamoyl group, a dimethylsulfamoyl group, a dibutylsulfamoyl group, an N,N-dimethylsulfamoyl group, an N,N-diethylsulfamoyl group or an N-cyclohexylsulfamoyl group), an arylsulfamoyl group (an arylsulfamoyl group having 6 to 12, preferably 6 to 8 carbon atoms, such as a phenylsulfamoyl group), or a carbamoylsulfamoyl group (a carbamoylsulfamoyl group having 1 to 12, preferably 1 to 6 carbon atoms, such as an N-(carbamoyl)sulfamoyl group);

a substituent having a substituent, which further has a substituent such as an alkoxyalkyl group (a straight, branched or cyclic alkoxyalkyl group having 1 to 32, preferably 1 to 12 carbon atoms, such as a methoxymethyl group, a methoxyethyl group, an ethoxyethyl group or a cyclohexyloxypropyl group), an alkoxyaryl group (an alkoxyaryl group having 7 to 18, preferably 7 to 12 carbon atoms, such as a p-methoxyphenyl group or a 2,4-dimethoxyphenyl group), a haloalkoxyaryl group (a haloalkoxyaryl group having 7 to 18, preferably 7 to 12 carbon atoms, such as a 2-chloro-4-methoxyphenyl group or a 2,5-dichloro-4-methoxyphenyl group), a hydroxyalkylthio group (a hydroxyalkylthio group having 1 to 15, preferably 1 to 6 carbon atoms, such as a hydroxyethylthio group or a 2-hydroxypropylthio group), or an alkoxycarbonylamino group (an alkoxycarbonylamino group having 2 to 10, preferably 2 to 6 carbon atoms, such as a methoxycarbonylamino group, an ethoxycarbonylamino group, a t-butoxycarbonylamino group or an isobutoxycarbonylamino group).

The total carbon number of substituents that the aromatic heterocyclic group and aryl group may have is 1 to 20 and more preferably, 1 to 8.

A and B of the general formula (1) each contain none of a carboxy group, a sulfo group and a quaternary ammonium group, more preferably contain none of a carboxy group, a sulfo group, a hydroxy group and a quaternary ammonium group. Examples of the carboxy group and sulfo group as mentioned above include not only acidic groups thereof but also neutral groups such as —COONa and —SO$_3$Na. More specifically, the triazene dissociative direct dye according to the present invention contains none of acidic type and neutral type carboxy groups, sulfo groups and quaternary ammonium groups.

The groups represented by A and B of the general formula (1) are each preferably derived from a diazo component. The diazo component used herein refers to a partial structure of a diazo compound (the diazo compound is converted from a heterocyclic compound or an aromatic hydrocarbon compound having an amino group as a substituent), which is an introducible moiety when the diazo compound is reacted with a coupling agent through a diazo coupling reaction. This concept is frequently used in the field of azo dyes. To describe in other words, the groups represented by A and B are each preferably a monovalent group obtained by removing an amino group from an amino-substituted heterocyclic compound or carbon aromatic compound, which can mediate a diazotization reaction.

Examples of the groups represented by A and B of the general formula (1) include aromatic heterocyclic groups represented by the following general formulas (AB-1) to (AB-32). In the general formulas below, symbol * indicates the site at which A and B bind to a triazene-1,3-diyl group, —N=N—NH—, in the general formula (1), and symbol "-" following the symbol * is an imaginary bond presumably formed when A and B bond to the triazene-1,3-diyl group. Reference symbols m and n each represent an integer from 0 to 4 and reference symbol l represents an integer from 0 to 5. $R_{11}$ to $R_{69}$ represents a hydrogen atom or the groups exemplified as substituents of A and B. The groups positioned next to each other may be bonded to form a saturated or unsaturated 5-membered or 6-membered structure,. Two or more groups represented by $R_{11}$ to $R_{69}$ present in a same group may be the same or different.

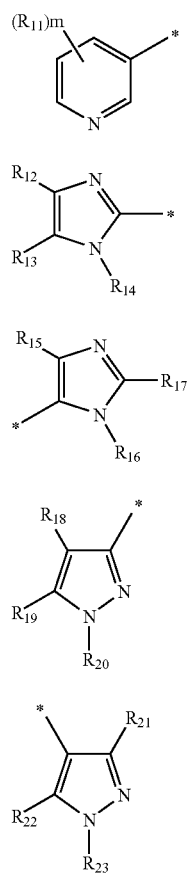

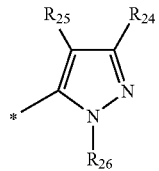

(AB-6)

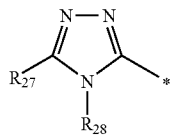

(AB-7)

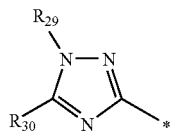

(AB-8)

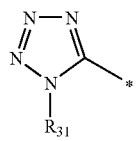

(AB-9)

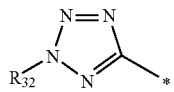

(AB-10)

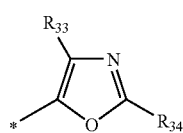

(AB-11)

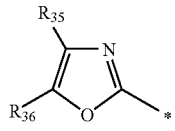

(AB-12)

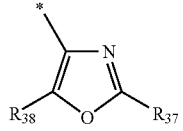

(AB-13)

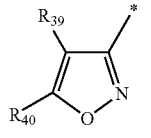

(AB-14)

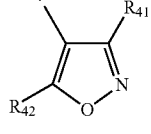

(AB-15)

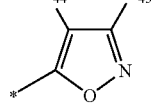

(AB-16)

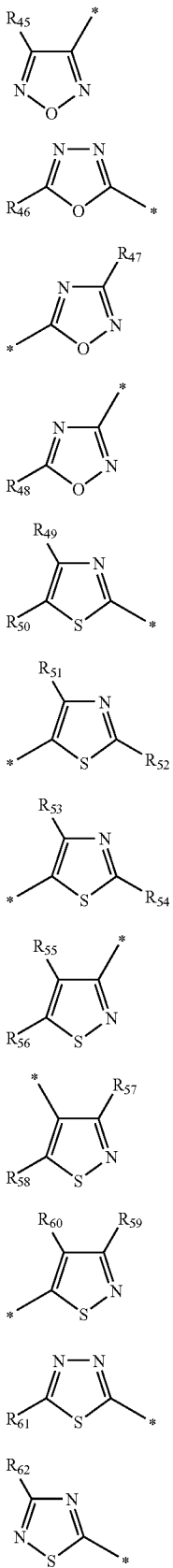

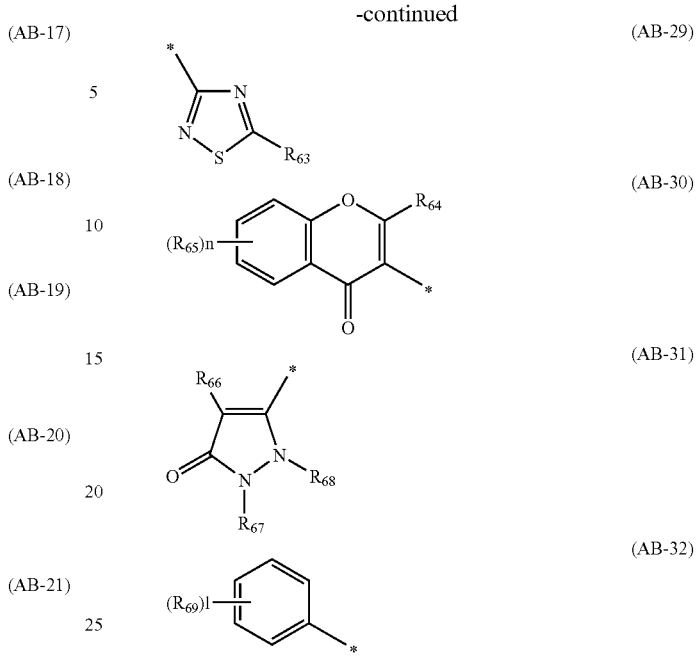

The groups represented by A and B are each preferably that represented by the general formula (AB-2), (AB-6), (AB-7), (AB-21), (AB-26), (AB-27), (AB-28) or (AB-29). Of them, the group represented by the general formula (AB-21), (AB-26), (AB-27) or (AB-28) is preferable.

The triazene compound represented by the general formula (1) is described in publications such as European Application Publication No. 71901 (1983); U.S. Pat. No. 3,431,251 (1969); Czechoslovakia Patent No. 181837 (1978); JP-B-49-027332; JP-B-40-017587; German Patent No. 796294 (1958); Chemical & Pharmaceutical Bulletin, 30(12), 4402-6 (1982)(A=B=1,2,4-thiadiazoles (where in a general formula (1), A=B=1,2,4-thiadiazoles (the same limitation will be applied to the following publications); Khimiko-Farmatsveticheskij Zhurnal, 14(9), 76-9 (1980)(A=B=isoxazoles); Magyar Kemiai Folyoirat, 84(10), 453-6 (1978) (A=B=coumarins); Journal of Heterocyclic Chemistry, 15(7), 1175-84 (1978) (A=B=pyrazoles); Chemische Berichte, 103(1), 112-22 (1970)(A=B=isothiazoles); Chemische Berichte, 103(6), 1805-14 (1970) (A=B=1,2,4-thiadiazoles); Khimiya Geterotsiklicheskikh Soedinenij, (3), 543-6 (1969) (A=B=imidazoles); Justus Liebigs Annalen der Chemie, 665, 144-9 (1963) (A=B=triazoles); Chemische Berichte, 93, 963-74 (1960) (A=B=1,2,4-thiadiazoles); and Helvetica Chimica Acta, 33, 1183-94 (1950) (A=B=pyrazolones).

In the triazene dissociative direct dye to be used in the hair dye composition according to the present invention, a pKa value of N—H of a triazene-1,3-diyl group represented by —N=N—NH— is preferably 1.0 to 9.0, more preferably, 2.0 to 7.0, and even more preferably, 2.0 to 5.0, in view of dyeing power of a dye. The pH value of the hair dye composition according to the present invention is preferably larger than the aforementioned pKa value. In this case, the triazene-1,3-diyl group is dissociated at N-H as shown in the following formula and the dissociated triazene direct dye imparts color firmly to hair.

In the triazene dissociative direct dye to be used in the hair dye composition according to the present invention, A and B of the general formula (1) are preferably the same 5-membered aromatic heterocyclic groups each containing at least one type of hetero atom selected from an oxygen atom, a sulfur atom and a nitrogen atom within the ring and optionally having a substituent.

Suitable examples of the triazene dissociative direct dye to be used in the hair dye composition according to the present invention include those represented by the following formulas D-1 to D-51 shown below.

-continued
D-15
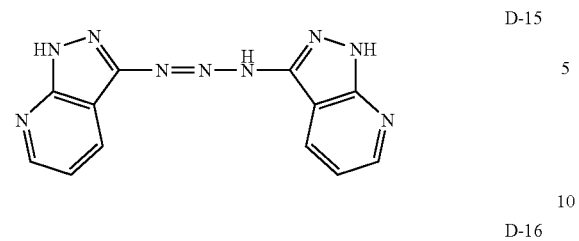
D-16
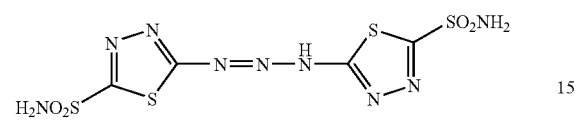
D-17
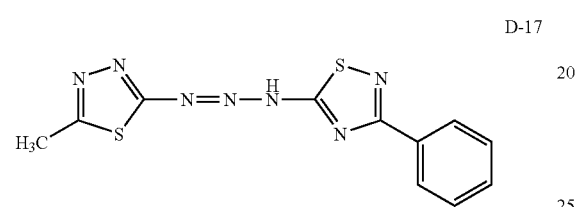
D-18
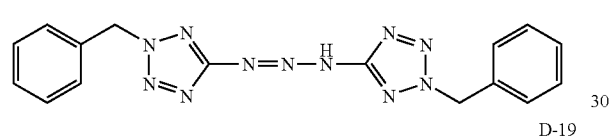
D-19
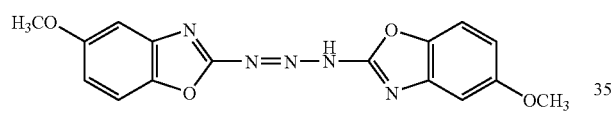
D-20
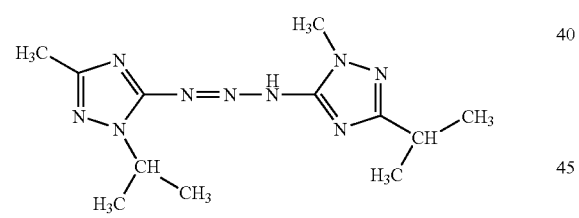
D-21
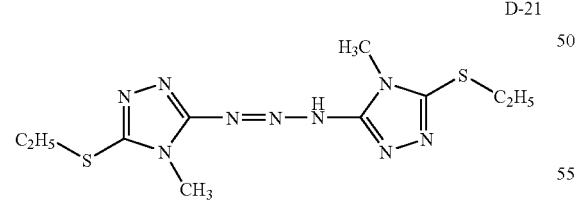
D-22
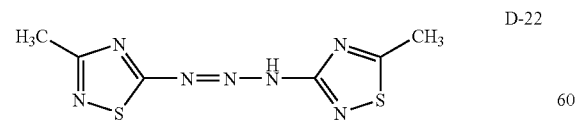
D-23
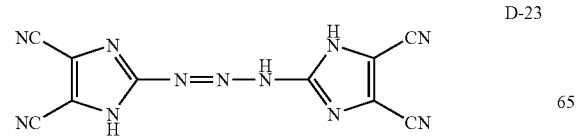
-continued
D-24
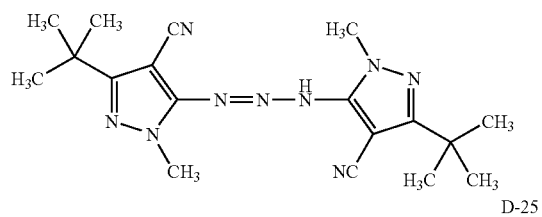
D-25
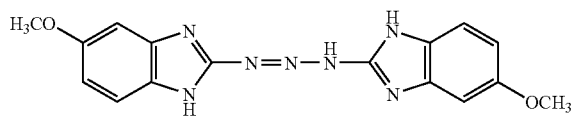
D-26
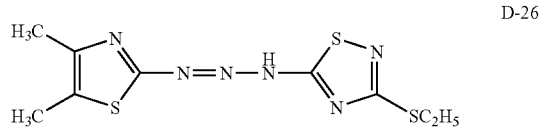
D-27
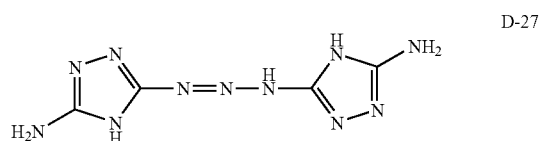
D-28
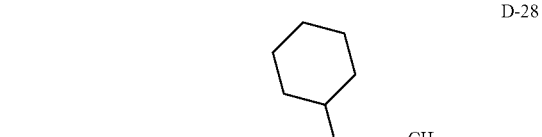
D-29
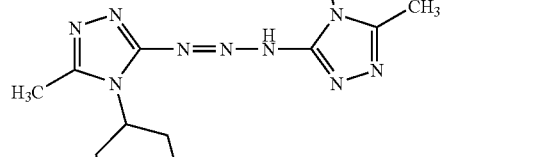
D-30
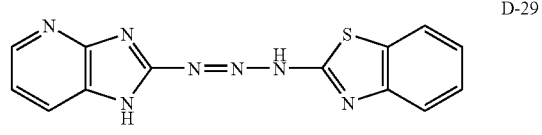
D-31
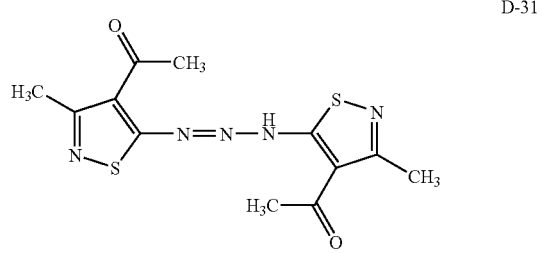

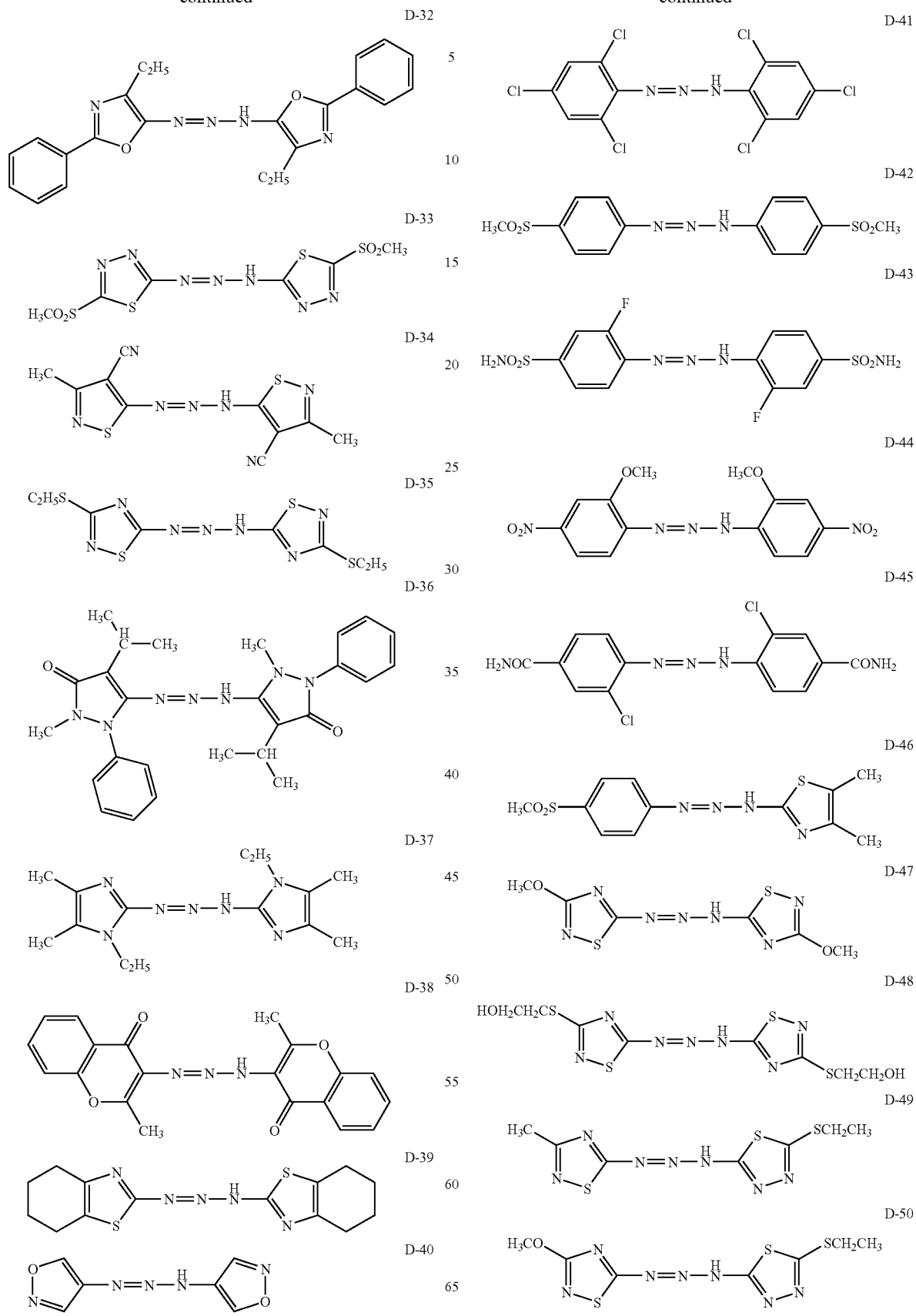

-continued

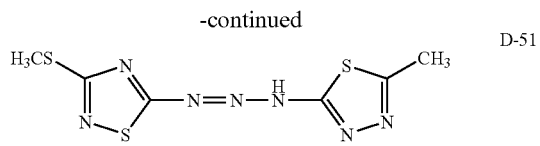
D-51

The triazene dissociative direct dyes may be used alone or in combination of two or more types. The content thereof is preferably 0.0001 to 20% by mass based on the total composition (the mixture of individual parts in the case of a two-part composition or a three-part composition) of the hair dye according to the present invention, more preferably, 0.001 to 20% by mass, even more preferably, 0.05 to 10% by mass, and even more preferably, 0.1 to 5% by mass.

The triazene dissociative direct dye to be used in the hair dye composition according to the present invention is excellent in storage stability within a broad pH range from 2 to 13 in which a hair dye composition is generally used. The hair dye composition of the present invention can be used in any pH value within the aforementioned range; however, preferably used at pH 5 or more in view of dyeability. Furthermore, since the triazene dissociative direct dye to be used in the present invention has high stability to an alkaline agent, the pH of the hair dye composition of the present invention can be set at 8 to 13, and more preferably, 9 to 12 in which high dyeability can be obtained. Even after it is stored for a long time, a triazene compound serving as a dissociative direct dye can maintain high dyeability without being decomposed. In the case where a hair dye composition is two-part composition or a three-part composition, the "pH" refers to a pH value of a mixture of them.

[Other Dyes]

The hair dye composition according to the present invention may contain another type of direct dye and an oxidation dye, thereby varying the color tone.

As the "another type" of direct dye, a direct dye known in the art may be used including an acid dye, a basic dye, a nitro dye, a dispersion dye and a cationic dye. Examples of the direct dye include Blue No. 1, Purple No. 401, Black No. 401, Orange No. 205, Red No. 227, Red No. 106, Yellow No. 203, Yellow No. 403 (1), acid Orange 3,2-nitro-p-phenylenediamine, 2-amino-6-chloro-4-nitrophenol, 3-nitro-p-hydroxyethylaminophenol, 4-nitro-o-phenylenediamine, 4-amino-3-nitrophenol, 4-hydroxypropylamino-3-nitrophenol, HC Blue 2, HC Orange 1, HC Red 1, HC Yellow 2, HC Yellow 4, HC Yellow 5, HC Red 3, N,N-bis(2-hydroxyethyl)-2-nitro-p-phenylenediamine, Dispersion Purple 1, Dispersion Blue 1, Dispersion Black 9, Basic Blue 99, Basic Brown 16, Basic Brown 17, Basic Red 76, Basic Yellow 76, Basic Yellow 57, Basic Orange 31, Basic Red 51 and methine-form cationic dye having a cyanine structure represented by the following formula.

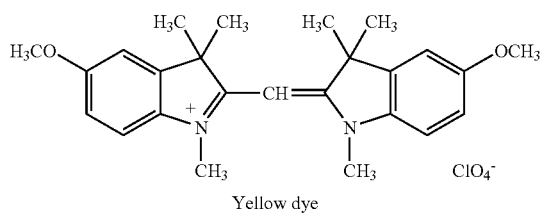
Yellow dye

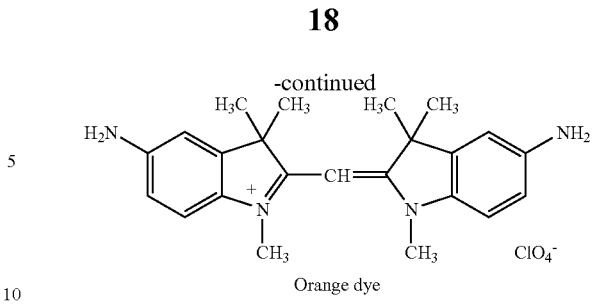
Orange dye

Furthermore, the direct dyes described in JP-A-2002-275040, 2003-107222, 2003-107223, 2003-113055, 2004-107343, 2003-342139 and 2004-155746 may be added to the examples.

When another type of direct dye is used in combination, the total content of another type of direct dye is preferably 0.001 to 20% by mass of the total hair dye composition of the present invention, more preferably 0.01 to 20% by mass, even more preferably 0.05 to 10% by mass, and even more preferably, 0.1 to 5% by mass.

When an oxidation dye is used, extremely vibrant and strong color, which cannot be imparted by a single use of the oxidation dye, can be imparted to hair. The oxidation dye can be used in combination with at least one type of known precursor and at least one type of coupler, which are usually used in an oxidation type hair dye.

Examples of the precursor include paraphenylenediamine, toluene-2,5-diamine, ortho-chloroparaphenylenediamine, N-phenyl paraphenylenediamine, N,N-bis(hydroxyethyl) paraphenylenediamine, 3-methyl-4-aminophenol, 2-hydroxyethylparaphenylenediamine, para-aminophenol, paramethylaminophenol, 4-amino-metacresol, ortho-aminophenol and salts thereof.

Examples of the coupler include resorcine, 2-methylresorcine, 1-naphthol, 1,5-dihydroxynaphthalene, 5-amino-ortho-cresol, meta-phenylenediamine, meta-aminophenol, 2,4-diaminophenoxyethanol, 2,6-diaminopyridine, 2-methyl-5-hydroxyethylaminophenol, 2-amino-3-hydroxypyridine and salts thereof.

As the precursor and coupler, two or more types of each of them are used in combination. The total content thereof is preferably 0.0005 to 20% by mass of the total composition, more preferably 0.001 to 19% by mass, even more preferably, 0.01 to 15% by mass, and even more preferably, 0.5 to 10% by mass.

To the hair dye composition according to the present invention, further an autooxidation dye, typically an indole or indoline, may be added.

The total content of the triazene dissociative direct dye represented by the general formula (1), another direct dye, oxidation dye and autooxidation dye is 0.001 to 20% by mass of the total composition, preferably 0.01 to 20% by mass, and more preferably, 0.5 to 15% by mass.

[Other Components]

When the hair dye composition according to the present invention is a two-part composition or a three-part composition, a first part contains an alkaline agent. Examples of the alkaline agent include ammonia and salts thereof; alkanolamines such as monoethanolamine, isopropanolamine, 2-amino-2-methylpropanol, and 2-amino butanol and salts thereof, alkanediamines such as 1,3-propanediamine, and salts thereof, and carbonates such as guanidine carbonate, sodium carbonate, potassium carbonate, sodium hydrogen carbonate, and potassium hydrogen carbonate. Of these alkaline agents, ammonia, alkanolamine and salts thereof are preferable. Preferable ammonium salts include ammonium carbonate, ammonium hydrogen carbonate. Preferable examples of the alkanolamine and the salts thereof include monoethanolamine and salts thereof.

These alkaline agents may be used in combination with two or more types. The content thereof is preferably 0.05 to 15% by mass, more preferably 0.1 to 10% by mass and even more preferably 0.2 to 5% by mass in view of sufficient dyeability and bleaching effect and reduction of hair damage and scalp irritation.

Since a triazene dissociative direct dye represented by the general formula (1) is extremely stable to an oxidizing agent, a mixture of the triazene dissociative direct dye and an oxidizing agent can be applied to hair. In other words, the hair dye composition according to the present invention may be a two-part composition composed of a first part containing a triazene dissociative direct dye represented by the general formula (1) and a second part containing an oxidizing agent. In this case, dyeing can be performed simultaneously with bleaching to obtain more vibrant color.

Examples of the oxidizing agent include hydrogen peroxide; persulfates such as ammonium persulfate, potassium persulfate and sodium persulfate, perborates such as sodium perborate, percarbonates such as sodium percarbonate, bromates such as sodium bromate and potassium bromate. Of them, hydrogen peroxide is preferable in view of bleaching properties to hair, stability and efficacy of a triazene dissociative direct dye represented by the general formula (1). Furthermore, another oxidizing agent serving as an auxiliary oxidizing agent may be used in combination with hydrogen peroxide. Of them, the combination of hydrogen peroxide and a persulfate is preferable.

The oxidizing agents may be used alone or in combination with two or more types. The content is preferably 0.5 to 30% by mass, and more preferably, 1 to 20% by mass of the total composition. When hydrogen peroxide is used in combination with a persulfate, the content of hydrogen peroxide is 0.5 to 10% by mass of the total composition and the content of the persulfate is 0.5 to 25% by mass of the total composition. The total content of both components is preferably 1 to 30% by mass.

When the hair dye composition according to the present invention is a two-part composition, the mixing ratio of a first part containing a triazene dissociative direct dye represented by the general formula (1) relative to a second part containing an oxidizing agent preferably falls within the range of 2:1 to 1:3 by volume.

In place of using an alkaline agent and an oxidizing agent themselves, use can be made of known oxidative hair dyes of a two-part composition and a three-part composition containing an alkaline agent or an oxidizing agent. More specifically, use can be made of a known two-part type oxidative hair dye composed of a first part containing an alkaline agent (that may optionally contain another known direct dye) and a second part containing an oxidizing agent; a known three-part type oxidative hair dye composed of a first part containing an alkaline agent (that may optionally contain another known direct dye), a second part containing an oxidizing agent, and a third part containing an auxiliary oxidizing agent. These two-part type oxidative hair dye and three-part type oxidative hair dye may be used in combination with a single-part type hair dye containing a triazene dissociative direct dye represented by the general formula (1), before use thereof or simultaneously therewith.

The hair dye composition according to the present invention may contain a suitable conditioning component applicable to hair. Examples of the conditioning component generally include a polymer or oil capable of being dissolved or dispersed in a hair dye composition and attachable to hair during rinsing or when diluted with water or shampoo.

When a conditioning component is used, the content thereof is 0.01 to 30% by mass, preferably 0.1 to 20% by mass, and more preferably, 0.1 to 10% by mass of the total composition.

Examples of the suitable conditioning component to be used in the hair dye composition according to the present invention include a conditioning agent characterized as a cationic polymer, silicone and an organic conditioning oil (such as hydrocarbon oil, polyolefin, fatty acid ester) and a combination of these, and further include a conditioning agent in which liquid particles are dispersed in an aqueous surfactant solution.

The cationic polymer refers to a polymer having a cationic group or a group capable of being ionized into a cationic group, and includes an amphoteric polymer having a cationic characteristic as a whole. More specifically, the cationic polymer is a polymer having an amino group or an ammonium group in a side chain of the polymer chain or an aqueous solution containing a diallyl-quaternary ammonium salt as a constitutional unit. Examples thereof include a cationized cellulose derivative, cationized starch, cationized guar gum derivative, a polymer or a copolymer of a diallyl-quaternary ammonium salt and a quaternary polyvinylpyrrolidone derivative. Of them, in view of effects such as softness and smoothness and compatibility with fingers during shampooing, hair-setting properties during drying and a moisture retention and in view of stability of the agent, use may be more preferably made of a polymer containing a diallyl-quaternary ammonium salt as a constitutional unit, a quaternary polyvinylpyrrolidone derivative and a cationized cellulose derivative are preferable, a polymer or copolymer of a diallyl-quaternary ammonium salt and a cationized cellulose derivative.

Specific examples of the polymer or copolymer of the diallyl-quaternary ammonium salt include dimethyldiallylammonium chloride polymer (polyquaternium-6, e.g., Merquat 100; Nalco Company), dimethyldiallylammonium chloride/acrylic acid copolymer (polyquaternium-22, e.g., Merquat 280 and 295; Nalco Company), dimethyldiallylammonium chloride/acrylamide copolymer (polyquaternium-7, e.g., Merquat 550; Nalco Company).

Specific examples of the quaternary polyvinylpyrrolidone derivative include quaternary ammonium salts (polyquaternium-11, e.g., Gafquat 734, 755, 755N (these are manufactured by ISP Japan Ltd.), which are obtained from a copolymer of vinylpyrrolidone (VP) and dimethylaminoethyl methacrylate and diethyl sulfate.

Specific examples of the cationic cellulose derivative include polymers of a quaternary ammonium salt (polyquartanium-10, such as Leoguard G, GP (these are manufactured by Lion Corporation), which are obtained by adding glycidyltrimethylammonium chloride to a hydroxyethylcellulose, polymer JR-125, JR-400, JR-30M, LR-400, LR-30M (these are manufactured by Amerchol Corporation), and hydroxyethylcellulose/dimethyldiallylammonium chloride copolymers (polyquartanium-4, such as cellquat H-100 and L-200 (these are manufactured by National Starch and Chemical Company).

Cationic polymers may be used in a combination of two or more types. The larger the content of a cationic polymer, the higher the effect is produced. However, when the content of a cationic polymer is excessively large, the stability decreases and the viscosity of the cationic polymer alone or the viscosity of a composition containing the cationic polymer decreases. In view of these points in combination with improvement of the feel of the hair, the content of a cationic polymer is preferably 0.001 to 20% by mass of the total composition, more preferably, 0.01 to 10% by mass, and even more preferably, 0.05 to 5% by mass.

The hair dye composition according to the present invention preferably contains a polysilicone to impart excellent sense of use. Examples of the polysilicone include a polyalkoxysilane and a modified silicone (such as amino modified silicone, fluorine modified silicone, alcohol modified silicone, polyether modified silicone, epoxy modified silicone or alkyl modified silicone). Preferably, a polyalkoxysilane and a polyether modified silicone and an amino modified silicone may be used.

As the polyalkoxysilane, a cyclic or noncyclic dimethylsiloxane polymer may be used. Examples thereof include SH200 series BY22-019, BY22-020, BY11-026, BY22-029, BY22-034, BY22-050A, BY22-055, BY22-060, BY22-083 and FZ-4188 (these are manufactured by Dow Corning Toray Co.), KF-9008, KM-900 series, MK-15H, and MK-88 (these are manufactured by Shin-Etsu Chemical Co. Ltd.).

As the polyether modified silicone, a silicone having a polyoxyalkylene group may be used. As a group constituting the polyoxyalkylene group may include an oxyethylene group and an oxypropylene group. Specific examples thereof include KF-6015, KF-945A, KF-6005, KF-6009, KF-6013, KF-6019, KF-6029, KF-6017, KF-6043, KF-353A, KF-354A and KF-355A (these are manufactured by Shin-Etsu Chemical Co. Ltd.), FZ-2404, SS-2805, FZ-2411, FZ-2412, SH3771M, SH3772M, SH3773M, SH3775M, SH3749, SS-280X series, BY22-008M, BY11-030 and BY25-337 (these are manufactured by Dow Corning Toray Co.,).

As the amino modified silicone, a silicone having an amino group or an ammonium group may be used. Examples thereof include amino modified silicone oil in which all or part of the terminal hydroxy groups is blocked by a methyl group or the like, and an amodimethicone whose terminals are not blocked. Preferable examples of the amino modified silicone include those represented by the general formula (2) below.

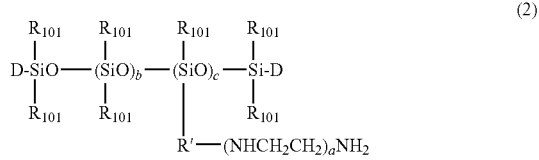

(2)

wherein $R_{101}$ represents a hydroxy group, a hydrogen atom or R; R represents a substituted or unsubstituted monovalent hydrocarbon group having 1 to 20 carbon atoms; D represents R, a group —R'—(NHCH$_2$CH$_2$)$_a$NH$_2$, a group OR, or a hydroxy group; R' represents a divalent hydrocarbon group having 1 to 8 carbon atoms; "a" represents an integer from 0 to 3, b and c represent the numbers, the total of them is not less than 10 to less than 20000, preferably not less than 10 to less than 3000, more preferably, not less than 30 to less than 1000, and even more preferably not less than 40 to less than 800 in terms of number average.

Preferable examples of commercially available amino modified silicone include amino modified silicone oils such as SF8452C, SS-3551(these are manufactured by Dow Corning Toray Co.), KF-8004, KF-867S, KF-8015 (these are manufactured by Shin-Etsu Chemical Co. Ltd.) and amodimethicone emulsions such as SM8704C, SM8904, BY22-079, FZ-4671 and FZ-4672 (these are manufactured by Dow Corning Toray Co.).

The total content of the silicone as mentioned above in the hair dye composition according to the present invention is preferably 0.02 to 40% by mass of the total composition, more preferably 0.1 to 20% by mass, and even more preferably, 0.2 to 15% by mass in view of obtaining a sufficient effect and suppressing greasiness.

When the silicone and the cationic polymer are contained in the hair dye composition according to the present invention, the ratio of the cationic polymer (active amount) to silicone in the total composition preferably falls within the range of 50:1 to 1:50, and more preferably, 50:1 to 1:10.

In the hair dye composition according to the present invention, a higher alcohol is preferably contained in at least one of the first, second and third parts, in view of improving the touch of hair and stability. The presence of the higher alcohol is effective since it forms a structure with a surfactant, preventing separation of the hair dye composition and improving feel of the hair during rinsing.

As the higher alcohol, an alcohol having 8 to 22 carbon atoms, and more preferably, 16 to 22 carbon atoms is used. Specific examples thereof include cetyl alcohol, stearyl alcohol, behenyl alcohol and a mixture thereof.

The higher alcohols may be used in combination with two or more types. The content thereof is preferably 0.01 to 20% by mass of the total composition, and more preferably, 0.1 to 10% by mass.

The hair dye composition according to the present invention may contain a surfactant. As the surfactant, any one of cationic surfactant, nonionic surfactant, amphoteric surfactant and anionic surfactant may be used.

As the cationic surfactant, mono long-chain alkyl quaternary ammonium salt is preferable. Specific examples thereof include cetyltrimethylammonium chloride, stearyl trimethylammonium chloride, aralkyltrimethylammonium chloride and behenyltrimethylammonium chloride. Of them, stearyl trimethylammonium chloride and behenyltrimethylammonium chloride are preferable.

Examples of the nonionic surfactant include a polyoxyalkylenealkyl ether, a polyoxyalkylenealkenyl ether, a higher fatty acid sucrose ester, a polyglycerin fatty acid ester, a higher fatty acid mono or diethanol amide, a polyoxyethylene hydrogenated castor oil, a polyoxyethylene sorbitan fatty acid ester, a polyoxyethylene sorbit fatty acid ester, an alkyl saccharide based surfactant, an alkylamine oxide and an alkylamideamine oxide. Of them, a polyoxyalkylenealkyl ether and a polyoxyethylene hydrogenated castor oil are preferable, and a polyoxyethylenealkyl ether is more preferable.

Examples of the amphoteric surfactant include imidazoline based, carbobetaine based, amidobetaine based, sulfobetaine based, hydroxysulfobetaine based and amidesulfobetaine based surfactants.

Examples of the anionic surfactant include an alkylbenzene sulfonate, an alkyl or alkenylether sulfonate, an alkyl or alkenylsulfate, an olefin sulfonate, an alkane sulfonate, a saturated or unsaturated fatty acid salt, an alkyl or alkenylether carboxylate, an α-sulfone fatty acid salt, an N-acylamino acid type surfactant, a phosphoric acid mono or diester type surfactant, and a sulfosuccinic acid ester. Examples of the alkylether sulfonate include a polyoxyethylene alkylether sulfonate. Examples of coupling ions of anionic residues of these surfactants include alkaline metal ions such as a sodium ion and a potassium ion; alkaline earth metal ions such as a calcium ion and a magnesium ion; an ammonium ion; and alkanol amines having 1 to 3 alkanol groups which has 2 or 3 carbon atoms (e.g., monoethanolamine, diethanolamine, triethanolamine and triisopropanolamine).

The surfactants may be used alone or in a combination of two or more types. The content thereof is not particularly limited and is, for example, 0.1 to 20% by mass of the total composition, preferably 0.1 to 18% by mass, and more preferably, 0.5 to 15% by mass.

In the hair dye composition according to the present invention, water or, if necessary, an organic solvent, is used as a medium. Examples of the organic solvent include lower fatty acid alcohols such as ethanol, propanol and isopropanol; aromatic alcohols such as benzyl alcohol and benzyloxy ethanol; polyols such as propylene glycol, 1,3-butanediol, diethylene glycol and glycerin; cellosolves such as ethylcellosolve and butylcellosolve; carbitols such as ethylcarbitol and butylcarbitol.

The content of the organic solvent is not particularly limited and is, for example, 0.05 to 20% by mass of the total composition, preferably, 0.1 to 15% by mass, and more preferably, 0.5 to 10% by mass.

The hair dye composition according to the present invention may contain, other than the aforementioned components, other optional components usually used as cosmetic materials. Examples of these optional components include a hydrocarbon, a fat and oil derived from animal or plant source, a higher fatty acid, a natural occurring or synthetic polymer, an ether, a protein derivative, a hydrolyzed protein, an amino acid, a preservative, a chelate agent, a stabilizer, an antioxidizing agent, a plant extract, a herbal medicine extract, a vitamin, a flavor and an ultraviolet absorber.

The hair dye composition according to the present invention may be provided as a single-part composition, two-part composition composed of a first part containing an alkaline agent and a second part containing an oxidizing agent such as hydrogen peroxide, or provided as a three-part composition further including a third part containing a powdery oxidizing agent formed of granules of a persulfate (such as ammonium persulfate, potassium persulfate or sodium persulfate) in combination.

Examples of the first part may take a form such as liquid, emulsion, cream, gel, paste or mousse or alternatively may take an aerosol form. In the case of a two-part (or three-part) composition, the form of the first and second parts may be a liquid, emulsion, cream, gel, paste or mousse form or alternatively, an aerosol form. When the first and second parts (first, second and third parts in the case of a three-part composition) are mixed, the mixture desirably has a viscosity sufficient to prevent dripping when applied to the hair. In the hair dye composition according to the present invention, the viscosity of the total composition in any one of the single-part composition, two-part composition or three-part composition is preferably 2000 to 100000 mPa·s at 25° C. as measured by a B type rotatory viscometer equipped with a helical stand (B8R viscometer, TOKIMEC Inc.). The viscosity herein is a value of the composition measured by a rotor T-C after being stirred at 10 rpm for one minute.

The hair dye composition according to the present invention can be used for dyeing hair by applying it to the hair. For example, hair is dyed by applying the hair dye composition according to the present invention adjusted to the aforementioned pH value (5 or more, preferably 8 to 13 and more preferably, 9 to 12) to hair such that the mass ratio of the dye composition to the hair is 0.1 to 10, allowing the hair to stand still for 1 to 60 minutes, and preferably, 10 to 40 minutes, washing away the hair dye composition of the present invention, and drying the hair.

The hair dye composition used herein preferably satisfies the aforementioned pH conditions (5 or more, preferably 8 to 13 and more preferably 9 to 12) during the period from application to hair to washing away.

The following examples further describe and demonstrate embodiments of the present invention. The examples are given solely for the purpose of illustration and are not to be construed as limitations of the present invention.

EXAMPLES

Synthesis Example 1

Triazene dissociative direct dye D-5 was synthesized in accordance with the following reaction scheme.

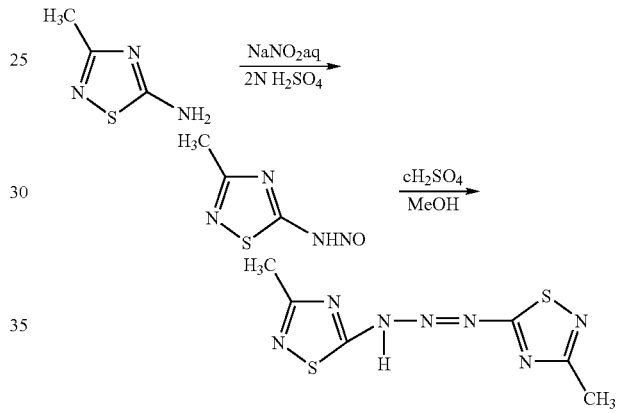

First, 11.5 g (0.1 mol) of 5-amino-3-methyl-1,2,4-thiadiazole was dissolved in 100 mL of 2N sulfuric acid. While the mixture was stirred, an aqueous sodium nitrite solution (containing 8.0 g (0.116 mmol) of sodium nitrite in 20 mL of water) was added dropwise to the mixture at 0° C. or less. After completion of dropwise addition, the resultant solution was continuously stirred further for one hour at 0° C. The crystals precipitated were collected by filtration and washed with ice cold water. The crystals were dried in the air at room temperature overnight to obtain 8.5 g (56% in yield) of 3-methyl-5-nitrosoamino-1,2,4-thiadiazole. Next, 7.2 g (0.05 mol) of the obtained thiadiazole was dissolved in 50 mL of methanol at room temperature. While the resultant solution was stirred, 3 mL of concentrated sulfuric acid was added dropwise to the solution at 5° C. or less. After completion of dropwise addition, the solution was continuously stirred further at 5° C. or less for one hour or less and at 15 to 20° C. for 2 hours. The crystals precipitated were collected by filtration. The crystals were recrystallized from methanol to obtain 2.5 g (41% in yield) of triazene dissociative direct dye D-5.

Synthesis Example 2

Triazene dissociative direct dye D-13 was synthesized in accordance with the following reaction scheme.

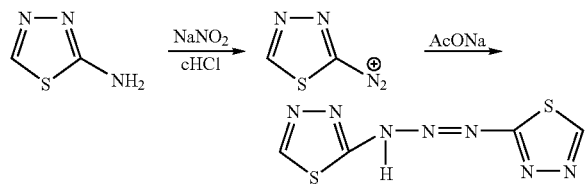

To 2.3 g of 2-amino-1,3,4-thiadiazole, concentrated hydrochloric acid (2.5 mL) and water (10 mL) were added. While the solution mixture was stirred at 5° C. or less, sodium nitrite (0.75 g) was added to the mixture. After the mixture was stirred for one hour, sodium acetate (1.65 g) was added to the mixture and stirred at 20° C. for 40 minutes. To the reaction solution, ice cold water was added to precipitate crystals, which were collected by filtration and washed with water. The crude crystals were recrystallized from ethanol to obtain 0.6 g (13% in yield) of triazene dissociative direct dye D-13.

Synthesis Example 3

Triazene dissociative direct dye D-49 was synthesized in accordance with the following reaction scheme.

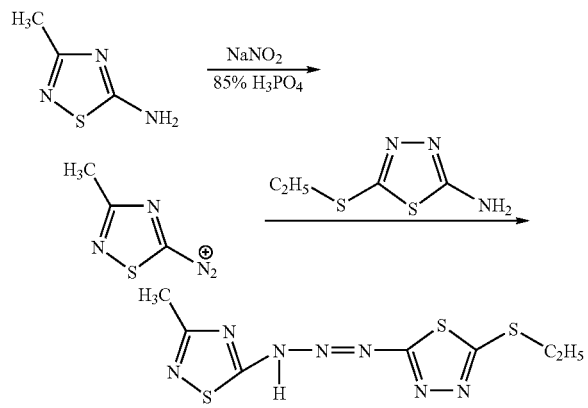

First, 11.5 g (0.1 mol) of 5-amino-3-methyl-1,2,4-thiadiazole was dissolved in 160 g of 85% phosphoric acid. While the mixture was stirred, 8.0 g (0.116 mmol) of sodium nitrite, which was divided into 4 portions, was added separately every 20 minutes at 0° C. or less. After completion of addition, the mixture was continuously stirred further at 5° C. or less for one hour. To the reaction solution, 16.15 g (0.1 mol) of 2-amino-5-ethylthio-1,3,4-thiadiazole, which was divided into portions, was added separately, and continuously stirred further at 5° C. or less for one hour and at 20 to 25° C. for one hour. To the reaction mixture, water (300 mL) was added to precipitate crystals, which were collected by filtration and washed with ice cold water. The crystals were recrystallized from ethanol to obtain 5.1 g (18% in yield) of triazene dissociative direct dye D-49.

Synthesis Example 4

Triazene dissociative direct dye D-34 was synthesized in accordance with the following reaction scheme.

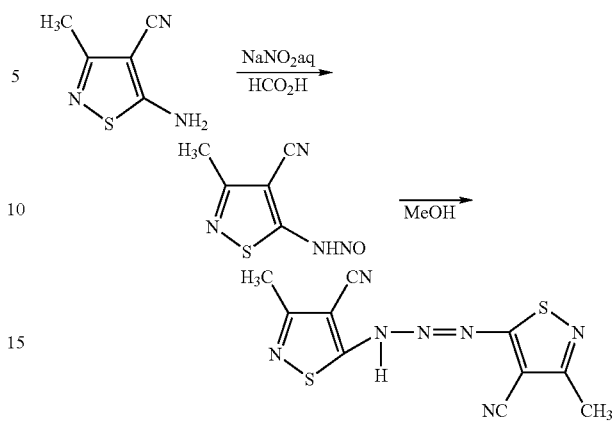

First, 4 g (0.028 mol) of 5-amino-4-cyano-3-methylisothiazole was dissolved in 40 mL of 98% formic acid. While the mixture was stirred, an aqueous sodium nitrite solution (containing 2.1 g (0.03 mmol) of sodium nitrite in 6 mL of water) was added dropwise at 0° C. or less. After completion of dropwise addition, the mixture was continuously stirred at 0° C. further for one hour. To the solution, 100 mL of water was added to precipitate crystals, which were collected by filtration and washed with ice cold water. The crystals were dried in the air at room temperature overnight to obtain 2.6 g (56% in yield) of 4-cyano-3-methyl-5-nitrosoaminoisothiazole. To 2 g (0.012 mol) of the obtained nitrosoaminoisothiazole, 20 mL of methanol was added, stirred while heating to an inner temperature of 55 to 60° C. for one hour and cooled to room temperature to precipitate crystals, which were collected by filtration. The crystals were recrystallized from methanol to obtain 0.66 g (41% in yield) of triazene dissociative direct dye D-34.

The other compounds below were synthesized in accordance with the same reaction schemes shown in Synthesis Examples 1 to 4.

TABLE 1

| Exemplified Compound No. | $\lambda$max (nm) | $\epsilon$max | Yield | Color | Synthetic method |
| --- | --- | --- | --- | --- | --- |
| D-5 | 415.0 | 16200 | 41% | Yellow | Synthesis Example 1 |
| D-13 | 434.0 | 17800 | 13% | Yellow | Synthesis Example 2 |
| D-17 | 435.0 | 18000 | 25% | Yellow | Synthesis Example 3 |
| D-31 | 437.0 | 17800 | 38% | Yellow | Synthesis Example 4 |
| D-34 | 452.0 | 21200 | 41% | Yellow | Synthesis Example 4 |
| D-35 | 420.0 | 16500 | 45% | Yellow | Synthesis Example 1 |
| D-47 | 412.0 | 15800 | 25% | Yellow | Synthesis Example 1 |
| D-48 | 421.0 | 16000 | 36% | Yellow | Synthesis Example 1 |
| D-49 | 432.0 | 17100 | 18% | Yellow | Synthesis Example 3 |
| D-50 | 430.0 | 16800 | 11% | Yellow | Synthesis Example 3 |
| D-51 | 431.0 | 17800 | 20% | Yellow | Synthesis Example 3 |

Examples 1 to 5

The hair dye compositions shown in Table 2 were prepared. The pH of the hair dye compositions obtained was measured by a glass electrode hydrogen ion concentration indicator (Type D-54, Horiba Ltd.). The hair dye compositions obtained were evaluated for following evaluation items 1 to 3.

TABLE 2

| (% by mass) | Example | | | | |
|---|---|---|---|---|---|
| | 1 | 2 | 3 | 4 | 5 |
| Triazene dye D-5 | 0.4 | 0.4 | 0.4 | 0.4 | 0.4 |
| Propanol | — | — | 5.0 | — | — |
| Isopropanol | 5.0 | 5.0 | — | — | 5.0 |
| Sodium carbonate | — | — | 2.0 | — | — |
| Ammonia | 1.25 | 1.25 | 0.84 | 0.84 | 1.25 |
| Hydrogen peroxide | — | 3.0 | 3.5 | 3.5 | 3.0 |
| Ammonium persulfate | — | — | — | — | 15.0 |
| Potassium persulfate | — | — | — | — | 7.0 |
| Purified water | Balance | Balance | Balance | Balance | Balance |
| pH | 11.3 | 10.3 | 10.3 | 10.1 | 9.1 |
| Total | 100.0 | 100.0 | 100.0 | 100.0 | 100.0 |

Evaluation 1: Coloring Performance

The hair dye compositions shown in Table 2 were each applied to an undamaged white goat hair bundle at 30° C. for 30 minutes. After completion of dyeing, each bundle was rinsed with water, shampooed and dried. In this manner, hair coloring process was performed. After the hair was dyed in this manner, the chromaticity of the hair bundle was measured. To explain more specifically, in each of Examples, the chromaticity of the hair bundle was measured by a color-difference meter, Type CR-400 (Konica Minolta Holdings, Inc) before and after the coloring process. The color specification value was indicated by a color coordinate system L*a*b*. The chroma saturation C* indicating vibrantness and a chromaticity change amount ΔE* were calculated in accordance with the following equation known in the art. The results are shown in Table 3.

$$C^* = \sqrt{(a^*)^2 + (b^*)^2}$$ [Mathematical formula 1]

$$\Delta E^* = \sqrt{(\Delta L^*)^2 + (\Delta a^*)^2 + (\Delta b^*)^2}$$ [Mathematical formula 2]

TABLE 3

| Example | L* | a* | b* | C* | ΔE* |
|---|---|---|---|---|---|
| 1 | 76 | −7 | 64 | 64 | 52 |
| 2 | 80 | −7 | 76 | 76 | 64 |
| 3 | 86 | −14 | 69 | 70 | 58 |
| 4 | 86 | −14 | 68 | 69 | 57 |
| 5 | 79 | −7 | 73 | 73 | 61 |
| Color of hair bundle before coloring | 83 | −1 | 13 | 13 | — |

As shown in Table 3, the value of chroma saturation C* after the coloring process was large in any one of Examples. It was demonstrated that vibrant color is imparted to the hair.

Evaluation 2: Light Fastness

After undamaged white goat hair bundles were dyed in the same manner as in Evaluation 1, chromaticity was measured in the same manner as in Evaluation 1. Subsequently, each of the hair bundles was irradiated with light of the entire wavelength range by a solar simulator for 72 hours and the chromaticity was measured again. Light fastness was evaluated by the chromaticity change amount ΔE* before and after light irradiation. The results are shown in Table 4.

TABLE 4

| Light fastness test | Treatment | L* | a* | b* | ΔE* |
|---|---|---|---|---|---|
| Test 1 | Before treatment | 76 | −7 | 64 | — |
| (Example 1) | After treatment | 75 | −7 | 63 | 1 |
| Test 2 | Before treatment | 86 | 14 | 69 | — |
| (Example 3) | After treatment | 86 | 13 | 65 | 4 |
| Test 3 | Before treatment | 86 | 14 | 68 | — |
| (Example 4) | After treatment | 84 | 14 | 65 | 4 |

As shown in Table 4, the chromaticity change amount ΔE* is small in any one of Examples. It was demonstrated that light fastness is satisfactory.

Evaluation 3: Fastness to Shampooing

After damaged white goat hair bundles (treated with a perm) were dyed in the same manner as in Evaluation 1, the chromaticity was measured in the same manner as in Evaluation 1. Subsequently, each of the hair bundles was shampooed by the steps of applying a shampoo (0.1 g) to hair (1 g) and rubbing the shampoo into the hair for 30 seconds, and rinsing the hair with water of 40° C. for 30 seconds. This process was repeated 20 times. Thereafter, the hair bundles were dried and the chromaticity of the hair bundles was measured by a color-difference meter, Type CR-400 (Konica Minolta Holdings, Inc.). The chromaticity change amount ΔE* before and after the shampooing step was regarded as fastness to shampoo and evaluated. The results are shown in Table 5.

TABLE 5

| Fastness test to shampoo | Treatment | L* | a* | b* | ΔE* |
|---|---|---|---|---|---|
| Test 4 | Before treatment | 76 | −7 | 64 | — |
| (Example 1) | After 20-time shampooing | 77 | −4 | 73 | 10 |

As shown in Table 5, the chromaticity change amount ΔE* is small. It was demonstrated that fastness to shampoo is satisfactory.

Formulation Examples 1 to 3

Single-part type hair dyes having the compositions shown in Table 6 were prepared in accordance with a customary method.

TABLE 6

| (% by mass) | Formulation example | | |
|---|---|---|---|
| | 1 | 2 | 3 |
| Triazene dye D-5 | 0.3 | — | 0.1 |
| Triazene dye D-13 | — | 0.2 | — |
| Triazene dye D-34 | — | — | — |
| Direct dye (E1)[*1] | — | 0.1 | — |
| Direct dye (E2)[*2] | — | — | 0.1 |
| HC Red 3 | 0.3 | — | 0.3 |
| Basic Yellow 57 | 0.1 | — | — |
| Basic Blue 99 | — | — | 0.1 |
| Ammonia (28% by mass) | 8.0 | 8.0 | 8.0 |
| Isopropanol | 1.5 | 1.5 | 1.5 |
| Ethanol | 6.0 | 6.0 | 5.0 |
| Benzyl alcohol | 8.0 | 8.0 | 8.0 |
| PEG-12 | — | — | 0.5 |
| Ammonium chloride | q.s.[*33] | q.s.[*3] | q.s.[*3] |
| Hydroxypropyl xanthan gum[*4] | 2.0 | 2.0 | 2.0 |
| PEG-9 dimethicone[*5] | — | 1.5 | 1.5 |

TABLE 6-continued

| (% by mass) | Formulation example | | |
|---|---|---|---|
| | 1 | 2 | 3 |
| Purified water | Balance | Balance | Balance |
| Total | 100.0 | 100.0 | 100.0 |

*[1] Direct dye represented by the following formula (hereinafter, the same reference will be used)
*[2] Direct dye represented by the following formula (hereinafter, the same reference will be used)
*[3] The amount to adjust pH to 10
*[4] Rhaball Gum EX, Sumitomo Pharmaceutical Co., Ltd.
*[5] KF-6005, Shin-Etsu Chemical Co. Ltd.

Direct Dye (E1)

Direct Dye (E2)

Single-part type hair dyes (Formulation Examples 1 to 3) are each applied in the same amount to hair to be dyed and allowed to stand still at 30° C. for 30 minutes. After the dye is rinsed away, the hair is shampooed and dried.

Formulation Examples 4 to 7

The first parts (cream form) of two-part hair dyes as shown in Table 7 and the common second part of the composition as shown in Table 8 are prepared by a customary method.

TABLE 7

| | Formulation example | | | |
|---|---|---|---|---|
| (% by mass) | 4 | 5 | 6 | 7 |
| Triazene dye D-17 | 0.5 | — | — | 0.1 |
| Triazene dye D-35 | — | 0.1 | — | — |
| Triazene dye D-48 | — | — | 0.3 | — |
| Triazene dye D-51 | — | — | — | 0.1 |
| Direct dye (E1) | — | 0.2 | 0.2 | — |
| Direct dye (E3)*[6] | — | 0.2 | — | — |
| Basic Orange 31 | — | — | — | 0.1 |
| Basic Red 51 | — | 0.1 | 0.2 | — |
| Orange No. 205 | — | — | 0.05 | — |
| Red No. 106 | 0.5 | — | — | — |
| Para-aminophenol | — | — | 0.1 | — |
| Toluene-2,5-diamine sulfate | — | — | — | 0.2 |
| 5-amino-orthocresol | — | — | — | 0.2 |
| Meta-aminophenol | — | — | 0.1 | — |
| Ammonia (28% by mass) | 6.0 | 6.0 | 6.0 | 6.0 |
| Stearyl alcohol | 8.0 | 8.0 | 8.0 | 8.0 |
| Cocamide MEA | 4.5 | 4.5 | 4.5 | 4.5 |
| Glyceryl stearate (SE) | 1.3 | 1.3 | 1.3 | 1.3 |
| Ceteareth-30 | 4.0 | 4.0 | 4.0 | 4.0 |
| Na lauryl sulfate | 1.0 | 1.0 | 1.0 | 1.0 |
| Oleic acid | 2.0 | 2.0 | 2.0 | 2.0 |
| PG | 1.5 | 1.5 | 1.5 | 1.5 |
| PEG-9 dimethicone*[7] | 1.5 | 1.5 | 1.5 | 1.5 |
| Hydrolyzed keratin | 0.5 | 0.5 | 0.5 | 0.5 |
| Panthenol | 0.8 | 0.8 | 0.8 | 0.8 |

TABLE 7-continued

| | Formulation example | | | |
|---|---|---|---|---|
| (% by mass) | 4 | 5 | 6 | 7 |
| EDTA-4Na | 0.5 | 0.5 | 0.5 | 0.5 |
| Ammonium chloride | q.s.*[8] | q.s.*[8] | q.s.*[8] | q.s.*[8] |
| Purified water | Balance | Balance | Balance | Balance |
| Total | 100.0 | 100.0 | 100.0 | 100.0 |

*[6] Direct dye represented by the following formula (hereinafter, the same reference will be used)
*[7] KF-6005, Shin-Etsu Chemical Co. Ltd.
*[8] The amount to adjust pH to 10

Direct Dye (E3)

TABLE 8

| (% by mass) | Common Second part |
|---|---|
| Cetanol | 2.0 |
| Na lauryl sulfate | 1.0 |
| Hydrogen peroxide (50% by mass) | 12.0 |
| Methylparaben | 0.1 |
| Phosphoric acid | Amount to adjust pH to 3.5 |
| Purified water | Balance |
| Total | 100.0 |

To the first part of each of the two-part type hair dyes (Formulation Examples 4 to 7), the common second part of the composition as shown in Table 8 is added in the same amount. The hair dye compositions are each applied to a hair bundle to be dyed in the same amount and allowed to stand still at 35° C. for 20 minutes. After each hair dye is rinsed away, the hair bundle is shampooed and dried.

Formulation Examples 8 to 12

The first parts (creamy form) of two-part type hair dyes are prepared by a customary method in accordance with the compositions shown in Table 9.

TABLE 9

| | Formulation example | | | | |
|---|---|---|---|---|---|
| (% by mass) | 8 | 9 | 10 | 11 | 12 |
| Triazene dye D-13 | 0.3 | — | 0.1 | — | 0.1 |
| Triazene dye D-47 | — | 0.3 | — | — | 0.1 |
| Triazene dye D-50 | — | — | 0.1 | 0.3 | — |
| Direct dye (E3) | — | 0.2 | — | — | 0.2 |
| Direct dye (E1) | — | — | — | 0.2 | — |
| HC Red 3 | — | — | 0.2 | — | 0.2 |
| Basic Blue 99 | — | — | 0.1 | — | — |

TABLE 9-continued

| (% by mass) | Formulation example | | | | |
|---|---|---|---|---|---|
| | 8 | 9 | 10 | 11 | 12 |
| Para-aminophenol | — | — | — | 0.1 | 0.1 |
| Toluene-2,5-diamine sulfate | 0.2 | 0.2 | — | — | 0.1 |
| 5-amino-orthocresol | — | 0.2 | — | — | 0.1 |
| Meta-aminophenol | 0.2 | — | — | 0.1 | 0.1 |
| Behentrimonium chloride | 2.1 | 2.1 | 2.1 | 2.1 | 2.1 |
| Mineral oil | 0.5 | 0.5 | 0.5 | 0.5 | 0.5 |
| PG | 7.0 | 7.0 | 7.0 | 7.0 | 7.0 |
| Cetearyl alcohol | 7.0 | 7.0 | 7.0 | 7.0 | 7.0 |
| Ammonia (28% by mass) | 6.5 | 6.5 | 6.5 | 6.5 | 6.5 |
| Polyquaternium-10*9 | 1.0 | — | 1.0 | — | 1.0 |
| Amodimethicone*10 | 1.5 | 1.5 | 1.5 | 1.5 | 1.5 |
| Ammonium Chloride | q.s.*11 | q.s.*11 | q.s.*11 | q.s.*11 | q.s.*11 |
| Purified water | Balance | Balance | Balance | Balance | Balance |
| Total | 100.0 | 100.0 | 100.0 | 100.0 | 100.0 |

*9 Ucare Polymer JR-400, Amerchol Corporation
*10 SM8704C, Dow Corning Toray Co.
*11 The amount to adjust pH to 10

To the first part of each of the two-part type hair dyes (Formulation Examples 8 to 12), the common second part of the composition as shown in Table 8 is added in the same amount. The hair dye compositions are each applied to a hair bundle to be dyed in the same amount and allowed to stand still at 30° C. for 30 minutes. After each hair dye is rinsed away, the hair bundle is shampooed and dried.

Formulation Examples 13 to 15

The first parts (creamy form) and third parts of three-part type hair dyes are prepared by a customary method in accordance with the compositions shown in Table 10.

TABLE 10

| | | Formulation example | | |
|---|---|---|---|---|
| (% by mass) | | 13 | 14 | 15 |
| First part | Triazene dye D-13 | 0.3 | 0.3 | — |
| | Direct dye (E1) | — | 0.05 | — |
| | Direct dye (E3) | — | 0.15 | 0.3 |
| | Ammonia (28% by mass) | 8.0 | 8.0 | 8.0 |
| | Stearyl alcohol | 8.0 | 8.0 | 8.0 |
| | Cocamide MEA | 4.5 | 4.5 | 4.5 |
| | Glyceryl stearate (SE) | 1.3 | 1.3 | 1.3 |
| | Ceteareth-30 | 4.0 | 4.0 | 4.0 |
| | Na lauryl sulfate | 1.0 | 1.0 | 1.0 |
| | Oleic acid | 2.0 | 2.0 | 2.0 |
| | PG | 1.5 | 1.5 | 1.5 |

TABLE 10-continued

| | | Formulation example | | |
|---|---|---|---|---|
| (% by mass) | | 13 | 14 | 15 |
| | PEG-9 dimethicone*12 | 1.5 | — | 1.5 |
| | Hydrolyzed keratin | 0.5 | 0.5 | 0.5 |
| | Panthenol | 0.8 | 0.8 | 0.8 |
| | EDTA-4Na | 0.5 | 0.5 | 0.5 |
| | Ammonium chloride | q.s.*13 | q.s.*13 | q.s.*13 |
| | Purified water | Balance | Balance | Balance |
| | Total | 100.0 | 100.0 | 100.0 |
| Third part | Triazene dye D-5 | — | 5.4 | 2.7 |
| | Triazene dye D-13 | — | — | 2.7 |
| | Ammonium persulfate*14 | 100.0 | 94.6 | 94.6 |
| | Total | 100.0 | 100.0 | 100.0 |

*12 KF-6005, Shin-Etsu Chemical Co. Ltd.
*13 The amount of adjust pH to 10
*14 Purity: 95% (powdery)

To the first part of each of the three-part type hair dyes (Formulation Examples 13 to 15), the common second part of the composition as shown in Table 8 is added in the same amount and the third part is added in a half amount of the first part. The hair dye compositions are each applied to a hair bundle to be dyed in the same amount and allowed to stand still at 30° C. for 20 minutes. After each hair dye is rinsed away, the hair bundle is shampooed and dried.

The invention claimed is:

1. A hair dye composition comprising a triazene dissociative direct dye represented by general formula (1):

$$A\text{-}N\!=\!N\text{---}NH\text{-}B \qquad (1)$$

wherein A and B are each a monocyclic or a bicyclic aromatic heterocyclic group that may have a substituent or a monocyclic or a bicyclic aryl group that may have a substituent and contain none of a carboxy group, a sulfo group and a quaternary ammonium group; and A and B each bind to a triazene-1,3-diyl group represented by —N=N—NH— via a carbon atom within A and B each, and A and B may be the same or different wherein the hair dyeing composition has a pH in the range of 8 to 13.

2. The hair dye composition according to claim 1, wherein A and B of the general formula (1) are the same 5-membered aromatic heterocyclic groups each containing at least one type of hetero atom selected from an oxygen atom, a sulfur atom and a nitrogen atom within the ring and optionally having a substituent.

3. A method of dyeing hair, comprising applying the hair dye composition according to claim 1 to hair.